(12) United States Patent
Massaro et al.

(10) Patent No.: US 11,602,124 B2
(45) Date of Patent: Mar. 14, 2023

(54) INSECT STORAGE AND DISPENSING SYSTEMS

(71) Applicant: Verily Life Sciences LLC, South San Francisco, CA (US)

(72) Inventors: Peter Massaro, San Carlos, CA (US); Nigel Snoad, Woodside, CA (US); Tiantian Zha, South San Francisco, CA (US); Craig Eldershaw, Belmont, CA (US); Martin Sheridan, Redwood City, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 230 days.

(21) Appl. No.: 16/588,125

(22) Filed: Sep. 30, 2019

(65) Prior Publication Data
US 2020/0107520 A1   Apr. 9, 2020

Related U.S. Application Data

(60) Provisional application No. 62/741,162, filed on Oct. 4, 2018.

(51) Int. Cl.
*A01K 1/08* (2006.01)
*A01M 99/00* (2006.01)

(52) U.S. Cl.
CPC .............. *A01K 1/08* (2013.01); *A01M 99/00* (2013.01)

(58) Field of Classification Search
CPC ..................... A01K 1/08; A01M 2200/012
See application file for complete search history.

(56) References Cited

U.S. PATENT DOCUMENTS 3,486,264 A * 12/1969 Lombard ............... A01K 79/00
43/4
3,711,987 A * 1/1973 Fisk ...................... A01M 3/005
43/134

(Continued)

FOREIGN PATENT DOCUMENTS

CN     202068849     12/2011
CN     204579619      8/2015
(Continued)

OTHER PUBLICATIONS

International Application No. PCT/US2019/053894, "International Search Report and Written Opinion", dated Feb. 7, 2020, 11 pages.
(Continued)

*Primary Examiner* — Monica L Perry
*Assistant Examiner* — Brittany A Lowery
(74) *Attorney, Agent, or Firm* — Kilpatrick Townsend & Stockton LLP

(57) ABSTRACT

Insect storage and dispensing system are described. An example system may include a dispensing container including at least one wall defining an interior volume for retaining a plurality of adult insects. The system may also include a piston that extends through a first opening of the dispensing container so as to expose a top face of the piston to the interior volume. Longitudinal movement of the piston toward a second opening of the dispensing container may dispense a portion of the plurality of insects from the dispensing container when the plurality of insects is retained in the dispensing container.

17 Claims, 6 Drawing Sheets

(56) References Cited

U.S. PATENT DOCUMENTS

| | | |
|---|---|---|
| 2008/0127549 A1 | 6/2008 | Russik |
| 2015/0264913 A1 | 9/2015 | Ganmor et al. |
| 2018/0206473 A1 * | 7/2018 | Massaro ............... A01M 1/106 |

FOREIGN PATENT DOCUMENTS

| | | | |
|---|---|---|---|
| CN | 108056080 | 5/2018 | |
| WO | WO-2017154004 A1 * | 9/2017 | ............... B64D 1/00 |
| WO | 2020072388 | 4/2020 | |

OTHER PUBLICATIONS

"Sterile Insect Technology—Research and Development.", <https://www.iaea.org/About/Policy/GC/GC50/GC50InfDocuments/English/gc50inf-3-att4_en.pdf> (2006).

* cited by examiner

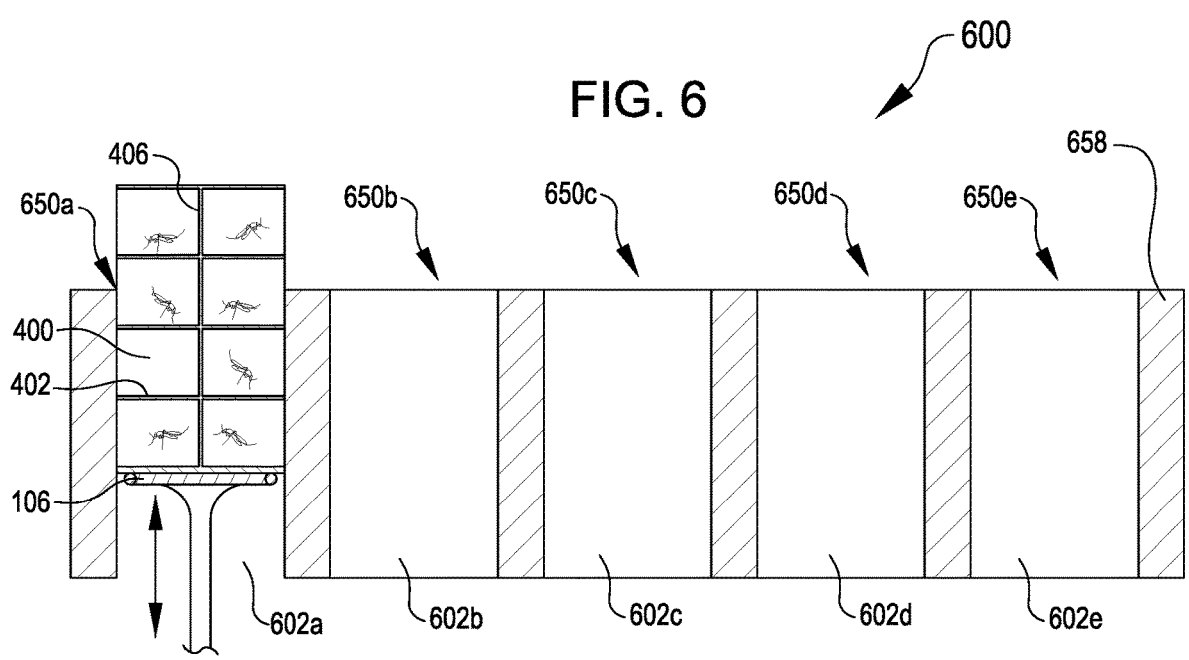

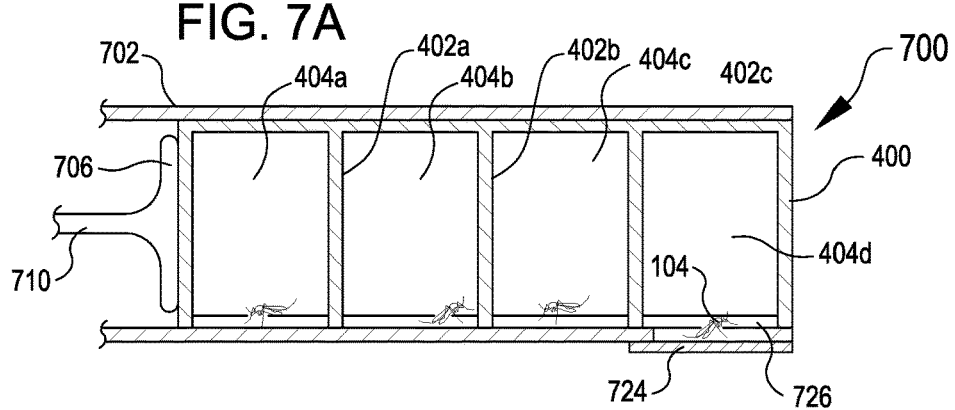
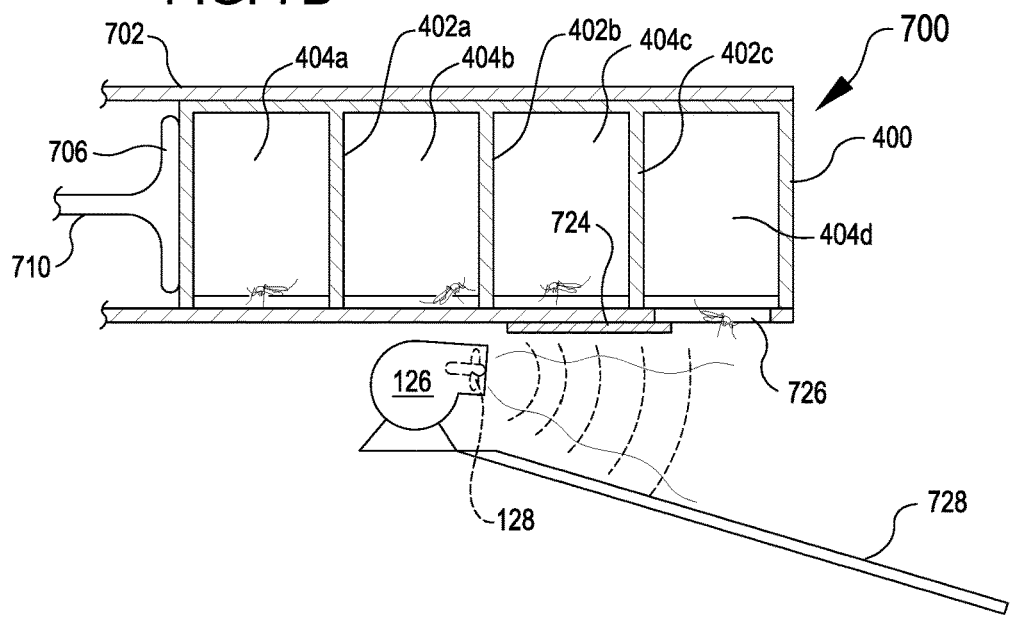
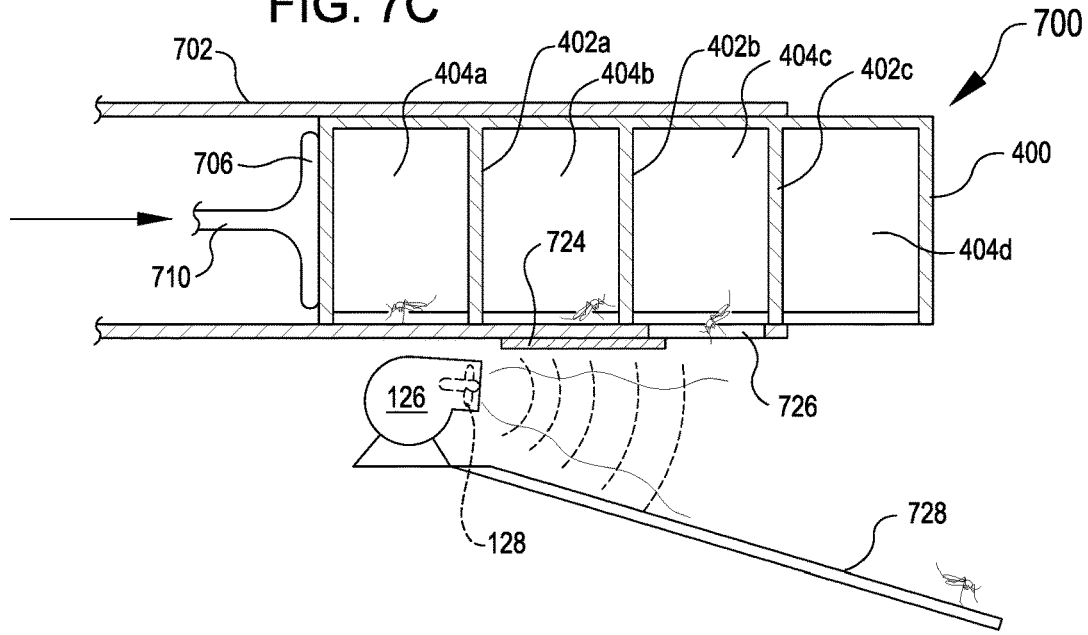

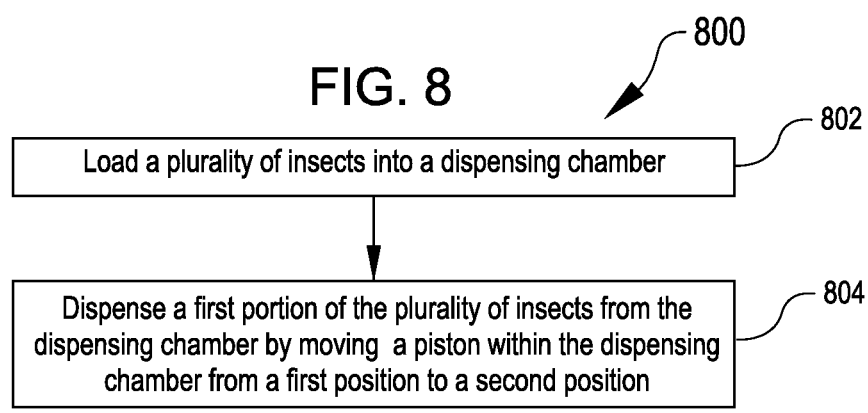
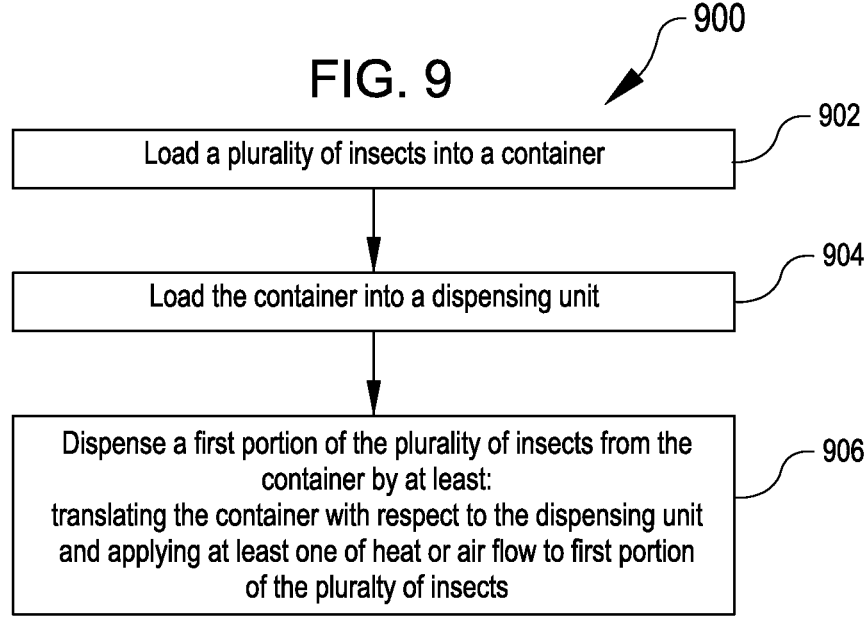
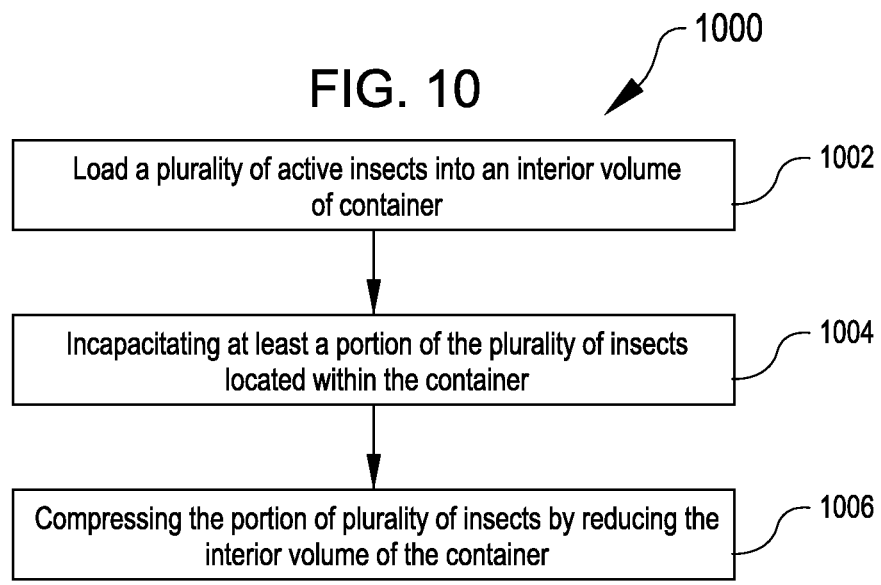

INSECT STORAGE AND DISPENSING SYSTEMS

CROSS-REFERENCE TO RELATED APPLICATION

This application claims the benefit of U.S. Provisional Application No. 62/741,162, filed Oct. 4, 2018, the subject matter of which is incorporated herein in its entirety by reference.

BACKGROUND

Insects can be chilled or otherwise sedated for packing and transportation. For example, as part of a Sterile Insect Technique (SIT) program, male insects may be chilled in a lab, loaded into a container, and transported to the field for release. Chilling insects increase packing densities as compared to approaches that pack active insects.

A conventional approach for releasing chilled insects from the container includes using an auger conveyor (e.g., a screw blade within a tube) to retrieve and dispense the insects from the container. Use of the auger conveyor, however, may create challenges. For example, the auger conveyor may lack accurate means for metering dispensing of the insects and results in crushing of an unsuitable number of insects between the screw blade and an interior wall of the tube. These challenges may result in prohibitively high damage or mortality rates resulting in low throughput and inconsistent dispensing rates.

SUMMARY

Various examples are described relating to insect storage and dispensing, systems for storing and dispensing insects, and methods for storing and dispensing insects.

In an example, a system is described. The system includes a dispensing container including at least one wall defining an interior volume for retaining a plurality of adult insects, the dispensing container including a first opening at a first end and a second opening at a second end opposite the first end. The system also includes a piston including a top face, the piston extending through the first opening and into the dispensing container so as to expose the top face to the interior volume, where longitudinal movement of the piston through the interior volume and toward the second opening dispenses a portion of the plurality of adult insects from the dispensing container when the plurality of adult insects is retained in the dispensing container. The system also includes an air movement system disposed adjacent the second opening of the dispensing container, the air movement system configured to cause an air stream to flow across the second opening to remove, from the dispensing container, portions of the plurality of adult insects that are presented at the second opening by the longitudinal movement of the piston.

In another example, a system is described. The system includes a plurality of elongate containers, each elongate container including a plurality of dividers arranged within the elongate container so as to define a plurality of compartments, each compartment of the plurality of compartments configured to retain a plurality of insects. The system also includes a dispensing system including a structure including a plurality of dispensing chambers, each dispensing chamber configured to receive an elongate container and dispense individual pluralities of insects from the plurality of compartments.

In yet another example, a method is described. The method includes loading a plurality of incapacitated insects into an interior volume of a dispensing chamber including an interior wall that defines the interior volume, at least a portion of the incapacitated insects in a chilled state. The method also includes dispensing a first portion of the plurality of incapacitated insects from the dispensing chamber by moving a piston through the interior volume from a first position to a second position.

In yet another example, a method is described. The method includes loading a plurality of incapacitated insects into a container. The method also includes loading the container into a dispensing chamber of a dispensing unit, the dispensing chamber including a first opening and a second opening; and dispensing a first portion of the plurality of insects from the container by at least. The method also includes translating the container with respect to the dispensing unit such that a leading portion of the container extends beyond the second opening. The method also includes applying at least one of heat or air flow to the first portion of the plurality of insects adjacent the second opening.

The illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 6 illustrates an insect dispensing system including a plurality of dispensing units arranged in a linear dispensing configuration, according to at least one example.

FIG. 6 illustrates an insect storage and dispensing system in a first state of operation, according to at least one example.

FIGS. 7A-7C illustrate an insect storage and dispensing system in a plurality of states of operation, according to various examples.

FIG. 8 illustrates an example process for dispensing a population of insects using an insect storage and dispensing system, according to at least one example.

FIG. 9 illustrates an example process for dispensing a population of insects using an insect storage and dispensing system, according to at least one example.

FIG. 10 illustrates an example process for loading a population of insects using an insect storage and dispensing system, according to at least one example.

DETAILED DESCRIPTION

Figure 1:
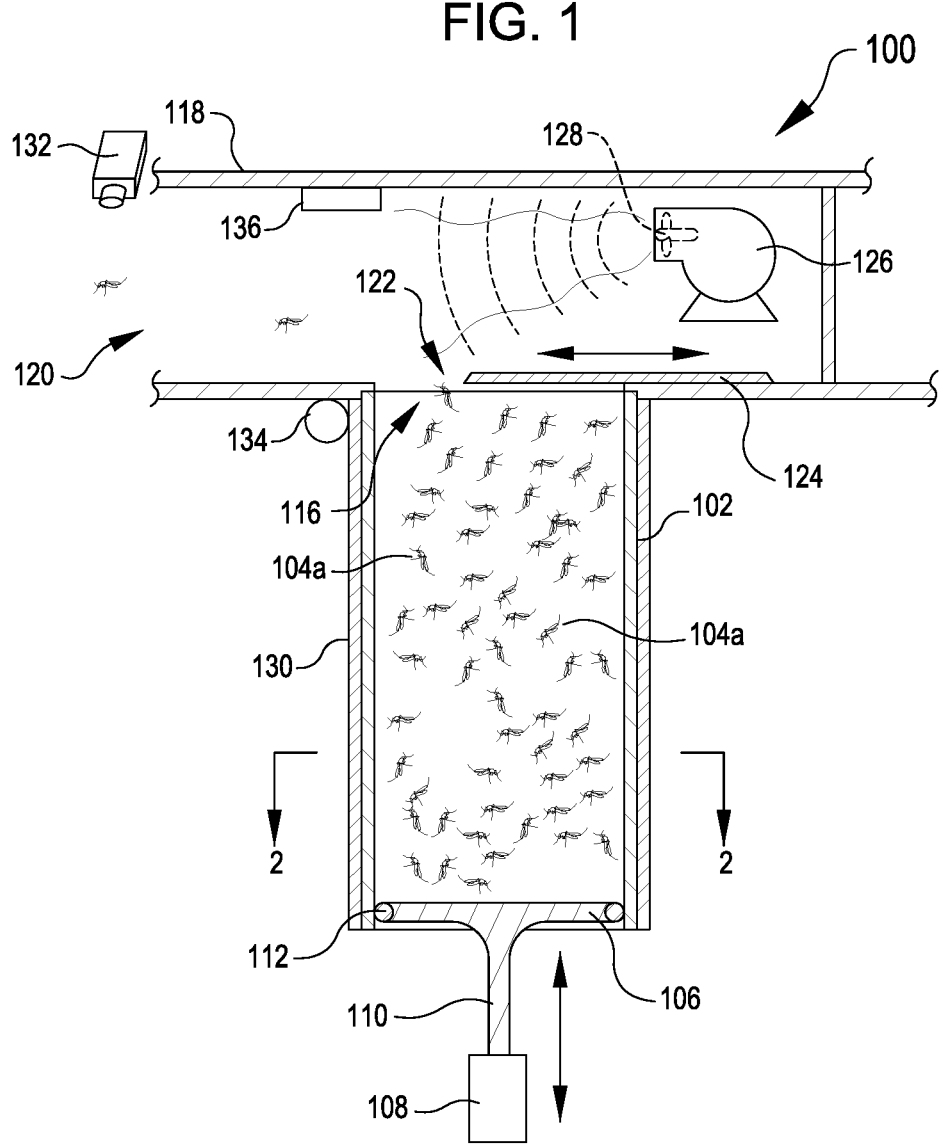
FIG. 1 illustrates an insect storage and dispensing system, according to at least one example.

Examples are described herein in the context of insect storage and dispensing systems for use in storing and dispensing of adult mosquitoes such as populations of *Aedes aegypti* or *Aedes albopictus* mosquitos. Those of ordinary skill in the art will realize that the following description is illustrative only and is not intended to be in any way limiting. For example, the insect storage and dispensing systems described herein can be used to store and dispense other species of mosquitoes (e.g., *Anopheles*) along with other insects such as, for example, screw-worm fly, Mexican fruit fly, Tsetse fly, Mediterranean fruit fly, Caribbean fruit fly, Queensland fruit fly, codling moth, pink bollworm, false codling moth, cactus moth, melon fly, onion fly, painted apple moth, and any other suitable insect. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a system for storing and dispensing insects is described. The insect storage and dispensing system may include a cylinder for receiving and storing chilled or otherwise sedated or incapacitated insects and/or for receiving a reusable cartridge that stores the chilled insects. The cylinder itself can also be chilled in order to maintain the insects in a chilled state. The insect storage and dispensing system may also include a piston installed in the cylinder and configured to translate within the cylinder. For example, a linear actuator may be operably coupled to a connecting rod of the piston and used to drive the piston in the cylinder. When the cylinder is loaded with insects, the piston can be driven toward an opening of the cylinder that is opposite a top face of the piston. In this manner, the piston may displace the insects and force them toward the opening. The opening can include a moveable gate that can be used to occlude all or a portion of the opening. Use of the gate can help to manage a dispensing rate of the insects. The insect storage and dispensing system can also include an air movement system, a revival system, and/or a vibration system disposed adjacent the opening. These system(s) can be positioned so as to blow insects, revive insects (e.g., using warm air, stimulants, Oxygen, etc.), and vibrate the insects at or around the time they are dispensed from the cylinder by the piston. This process of blowing, reviving, and/or vibrating the insects functions to both revive the insects and remove them from the cylinder. Once out of the cylinder, the insects can be directed (e.g., using the air movement system and/or vibration system) and/or can naturally make their way through an outlet and into the wild.

This illustrative example is given to introduce the reader to the general subject matter discussed herein and the disclosure is not limited to this example. The following sections describe various additional non-limiting examples of insect storage and dispensing systems.

Referring now to FIG. 1, FIG. 1 illustrates an insect storage and dispensing system 100, according to at least one example. The insect storage and dispensing system 100 includes a dispensing chamber 102 (e.g., any suitable container) for holding insects 104 such as adult insects. For example, as illustrated in the dispensing chamber 102, the insects 104 can be densely packed into the dispensing chamber 102. Such dense packing may be possible, for example, by chilling or otherwise sedating the insects 104 as part of loading them into the dispensing chamber 102 and/or by transferring previously chilled insects 104 to the dispensing chamber 102. For example, some combination of chilling and/or oxygen deprivation may be used to sedate the insects 104. In one particular example, oxygen deprivation may be used for fast knock down, then the insects 104 may be chilled. To revive the insects 104 at a later time, oxygen and/or heat may be added. In some examples, the chilling keeps the insects 104 unconscious for extended periods without lasting damage.

As introduced above, the dispensing chamber 102 itself may be configured to chill the insects 104. For example, the dispensing chamber 102 may include a cooling sheath 130 that extends around all or a portion of the dispensing chamber 102. In some examples, the cooling sheath 130 may be integrated into the walls of the dispensing chamber 102. The cooling sheath 130 can be configured to cool the dispensing chamber 102 by using refrigeration and any other suitable approach.

The insect storage and dispensing system 100 includes a piston 106 configured to travel within the dispensing chamber 102. For example, the dispensing chamber 102 may be elongate and the piston 106 can travel within the chamber 102 to change the volume of the chamber 102. In this example, the piston 106 is connected to an actuator device 108 via a connecting rod 110. The actuator device 108 may be any suitable motor, servo, or other device configured to drive the piston 106 via the connecting rod 110. For example, the actuator device 108 can include a linear actuator that is configured to move the piston 106 up and down within the dispensing chamber 102. In other examples, the actuator device 108 can include a rotary actuator connected to the connecting rod 110 and configured to drive the piston 106. In some examples, the actuator device 108 may be computer controlled and/or may be manually controlled. In some examples, the piston 106 is driven manually (e.g., a human worker can push and pull on the connecting rod 110 to move the piston 106 within the dispensing chamber 102). The dispensing chamber 102 and the piston 106 can have any suitable matching profile such as circular, square, rectangular, triangular, ovate, elliptical, and any other profile.

In some examples, the insect storage and dispensing system 100 is implemented using dispensing cartridges as will be described in more detail below (e.g., with respect to FIGS. 4 and 5). For example, the insects 104 may be loaded into dispensing cartridges which may then be loaded into the dispensing chambers 102. Removing the insects 104 from a dispensing cartridge may include causing the entire dispensing cartridge to translate with respect to the dispensing chamber 102 and/or causing an interior portion of the dispensing cartridge to translate with respect to the dispensing chamber 102.

Figure 2:
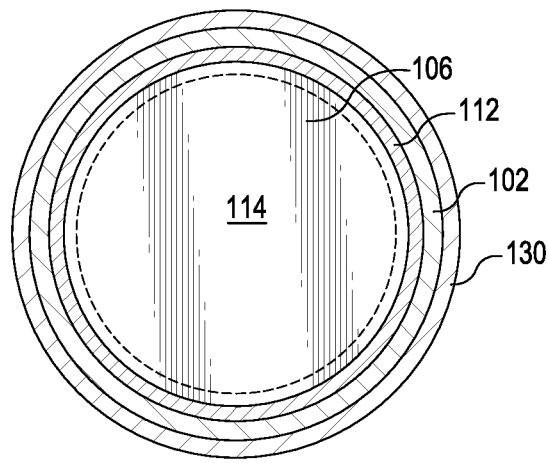
FIG. 2 illustrates a cross-sectional view of the insect storage and dispensing system of FIG. 1, according to at least one example.
Figure 3:
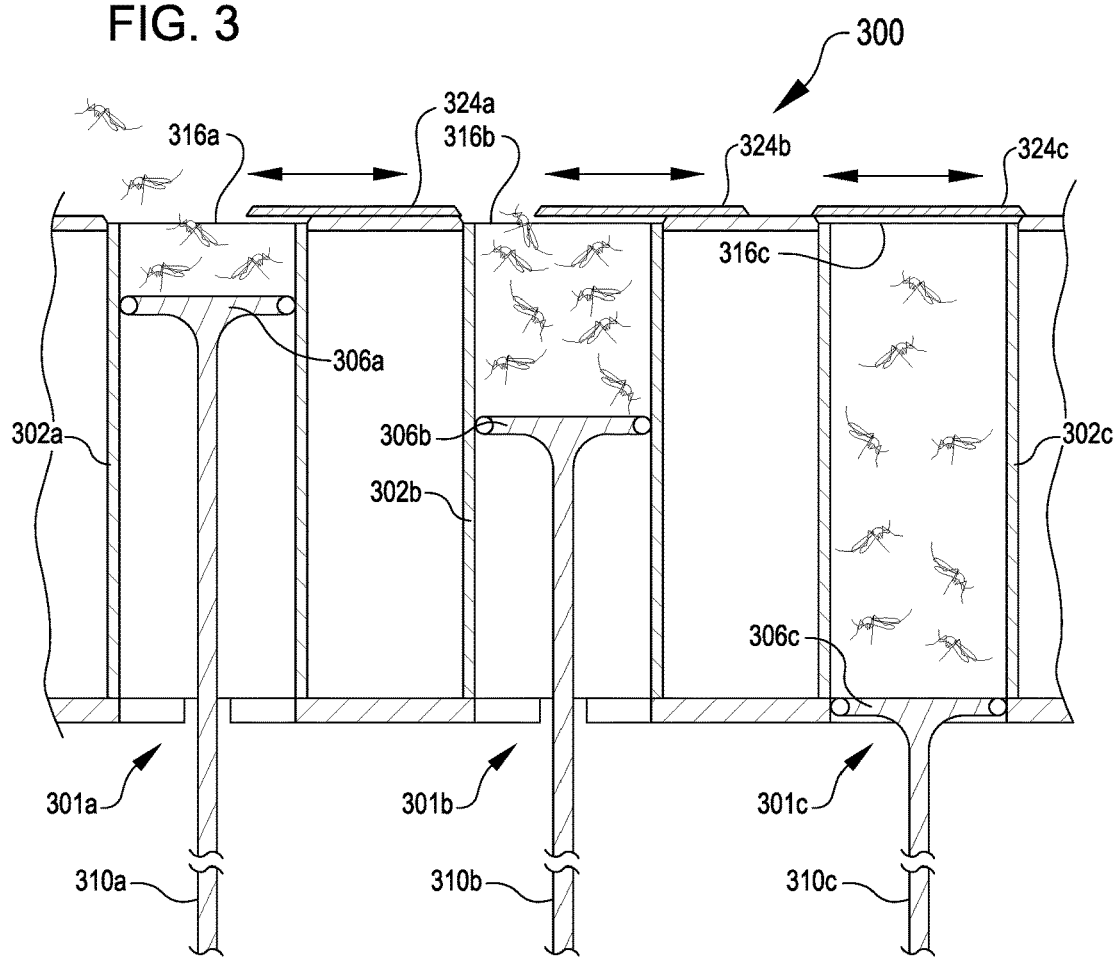
FIG. 3 illustrates an insect storage and dispensing system including a plurality of dispensing chambers, according to at least one example.

As illustrated in FIG. 2, which is a cross-sectional view of the piston 106 and the dispensing chamber 102, the piston 106 can also include a top face 114 and a flexible piston ring 112. The flexible piston ring 112 can be used to maintain a tight seal between inner walls of the dispensing chamber 102 and the piston 106. In some examples, the flexible piston ring 112 is formed from a rubber O-ring, a thin metal ring, an array of soft bristles, or other flexible material. The combination of the piston 106 and flexible piston ring 112 may enable displacing the insects 104 with minimal crushing of insects within the chamber 102. The top face 114 of the piston 106 is exposed to an inner volume of the dispensing chamber 102. The insects 104 are pushed toward an opening of the dispensing chamber 102 by the top face 114 as the piston 106 is driven toward a top chamber opening 116.

The insect storage and dispensing system 100 also includes an exit chamber 118 to receive insects from the dispensing chamber 102 and provide a pathway for the insects to traverse to an external environment. The exit chamber 118 is disposed adjacent the top chamber opening 116 of the dispensing chamber 102. In some examples, the exit chamber 118 is a box, a cylinder, or other structure. In the illustrated example, the exit chamber 118 is a cylinder having an inlet 122 and an outlet 120. The exit chamber 118 is mounted perpendicularly to the dispensing chamber 102 to connect the top chamber opening 116 to the inlet 122 and provide a pathway from the chamber 102 to the exit chamber 118. And while the exit chamber 108 is a cylinder in this example, it may be any suitable shape or cross-section according to other examples.

The insect storage and dispensing system 100 also includes an insect counting system 132. The insect counting system 132 is configured to count insects, classify insects, and/or detect a rate of release. The insect counting system 132 includes one or more sensors such as a camera, a microphone, a ultrasonic Doppler sensors, and/or a light sensor configured to detect insects 104 as they exit through the outlet 120. For example, the insect counting system 132 can include an array of light-emitting diodes (LEDs) for illuminating the insects 104 and light sensors for differentiating the insects 104. In some examples, the insect counting system 132 uses a combination of acoustic and optical sensors (e.g., one or more pseudo-acoustic optical sensors) to count, detect rate of release, and/or classify the insects 104.

The insect storage and dispensing system 100 also includes a gate 124 that can be opened, closed, or partially opened to block the inlet 122 into the exit chamber 118. In some examples, the gate 124 may be slidable or otherwise moveable to selectively occlude more or less of the area of the top chamber opening 116 to increase or decrease the size of the opening into the inlet 122 and restrict movement of insects from the chamber 102 into the exit chamber 118. In some examples, the gate 124 is a trap-door configuration. In some examples, the piston 106 may include a rod that extends upwards through the dispensing chamber 102, ending in a plate so that when the piston 106 is fully retracted, the plate entirely blocks the chamber opening 116, but as the piston 106 moves up, it moves the plate away from the chamber opening 116, allowing the insects 104 to escape.

The area of the inlet 122, which may be defined by the position of the gate 124, may determine a dispensing rate of the insects 104 (e.g., a rate at which the insects 104 are removed from the dispensing chamber 102 and introduced into the field via the outlet 120). In some examples, the translation rate of the piston 106 may also be used to determine the dispensing rate of the insects 104. The dispensing rate of the insects 104 may also depend on the mode of distribution. For example, a possible dispensing rate for a backpack distribution system may be around 50-100 insects per second. A possible dispensing rate for an airborne distribution system (e.g., from an aerial vehicle) may be around 1000 insects per second. The dispensing rate may also be increased by increasing the cross-sectional area of the dispensing chamber 102 and/or by adding additional dispensing chambers 102 to the system 100. For example, two or more dispensing chambers 102 may be arranged to dispense insects 104 into the exit chamber 118.

In some examples, the insect storage and dispensing system 100 also includes one or more systems and/or devices configured to move and/or revive the insects 104 as they leave the system 100 and to otherwise control conditions present in the system 100. For example, the insect storage and dispensing system 100 can include an air movement system 128, a revival system 126, a humidity control system 136, and a vibration system 134.

The air movement system 128 includes a fan, a Venturi tube, an aspirator device (e.g., a vacuum that aspirates a thin sheet of insects 104), an air nozzle connected to a compressed air source, or any other suitable system that blows air and/or creates an air vacuum. For example, the air movement system 128 can include a fan mounted in the exit chamber 118. The air movement system 128 can also include a fan mounted outside the exit chamber 118 and including a duct into the exit chamber 118. When dispensing the insects 104 from the dispensing chamber 102, the fan may direct an air stream sideways across the top chamber opening 116. This air stream can function to remove insects 104 from the dispensing chamber 102.

As an additional example, the insect storage and dispensing system 100 can be mounted to a moving vehicle (e.g., a car, golf cart, aerial vehicle, etc.) and the air movement system 128 can include a Venturi tube extending between the exit chamber 118 and side or front exterior surface of the vehicle. As the vehicle moves, an air stream will be directed into the Venturi tube and across the top chamber opening 116. This air stream can function to remove insects 104 from the dispensing chamber 102.

When the air movement system 128 includes an aspirator device, air suction can be used to remove the insects 104 from the dispensing chamber 102. The air suction will effectively "pull" the insects 104 through the inlet 122.

The revival system 126 can include a heater (e.g., electric heater) and blower to regulate the air temperature in the exit chamber 118 to be greater than the dispensing chamber 102. In other examples, the revival system 126 may also warm the dispensing chamber 102. For example, a top portion of the dispensing chamber 102, adjacent the exit chamber 118, may be warmed using the revival system 126. As the insects 104 from the dispensing chamber 102 are moved toward warmer areas (e.g., the exit chamber 118 and/or a top portion of the dispensing chamber 102), the insects 104 may begin to warm and "wake up" (e.g., transition from a sedated state to an active state). In some examples, this may include waking up a first layer of insects 104 present in the dispensing chamber 102. In some examples, the insects 104 will transition from the sedated state (e.g., as in the dispensing chamber 102) to an active state at some point in time between when the insects exit the dispensing chamber 102 via the top cylinder opening 116. For example, some insects 104 may transition while in the exit chamber 118. Other insects 104 may transition at some point after exiting the exit chamber 118 via the outlet 120. For example, it may be desirable for the insects 104 to transition while falling from the outlet 120 but before hitting the ground below the insect storage and dispensing system 100. When the insect storage and dispensing system 100 is mounted in an aerial vehicle, the time for transitioning outside of the exit chamber 118 may be greater than if the insect storage and dispensing system 100 is mounted to a person's backpack.

The revival system 126 can also operate based on principles of radiant heat. For example, an interior surface of the exit chamber 118 may be warmed using radiant heating such that heat radiates within the exit chamber 118 and warms not only the interior surface, but also the air in the exit chamber 118.

In some examples, the revival system 126 and the air movement system 128 may be combined into one device that warms the air and blows the warmed air to both move and warm/revive the insects 104.

In some examples, the revival system 126 also includes a gas distribution system to assist in unloading and/or reviving the insects 104. For example, the gas distribution system can be configured to output Nitrogen, Oxygen, or other suitable stimulant to enhance revival of the insects 104. In some examples, the gas distribution system can be used in conjunction with the air movement system 128. For example, the air movement system 128 can blow gas distributed by the gas distribution system of the revival system 126.

The humidity control system 136 includes any suitable device and/or system configured to affect humidity of the system 100. For example, the humidity control system 136 can be configured to provide active or passive humidification or dehumidification. Humidity control may be desirable during temperature changing in order to avoid dehydration of the insects 104 and/or excessive condensation within the system 100. Thus, the humidity control system 136 or some variation thereof may be used when the insects 104 are loaded into the system 100 and sedated to control condensation. At revival (e.g., when heat is applied), the humidity control system 136 may be used to control condensation and dehydration. The vibration system 134 is configured to apply vibration to assist in the revival and/or removal of the insects 104 from the insect storage and dispensing system 100. For example, the vibration system 134 can include one or more vibration motors (e.g., an eccentric rotating mass vibration motor, a linear resonant actuator, or other motor in any suitable form factor) that are configured to apply vibration to the insects 104 within the exit chamber 118 and/or within the chamber 102. For example, the vibration system 134 can be mounted adjacent the outlet 120 of the exit chamber 118 and/or adjacent the inlet 122 of the exit chamber 118. In some examples, the vibration system 134 includes more than one vibration device to provide targeted vibration within the system 100.

FIG. 3 illustrates an insect storage and dispensing system 300 including a plurality of dispensing units 301, according to at least one example. Each dispensing unit 301 may include similar features as discussed with reference to the insect storage and dispensing system 100. For example, each dispensing unit 301 may include a dispensing chamber 302, a piston 306, a connecting rod 310, and a gate 324. The function of the dispensing units 301 may be similar to the function described with reference to the insect storage and dispensing system 100 shown in FIG. 1. The insect storage and dispensing system 300 can also include an exit chamber including multiple inlets corresponding to top cylinder openings 316. In some examples, the exit chamber includes one or more outlets. The insect storage and dispensing system 300 can also one or more systems and/or devices configured to move and/or heat the insects 104, such as air movement devices and/or heaters. The insect storage and dispensing system 300 can also include actuator devices to drive the pistons 306 via the connecting rods 310, such as described above with respect to FIG. 1. The dispensing units 301 may be disposed in a linear array, two-dimensional array, rotary array, or any other suitable arrangement.

In some examples, each of the dispensing units 301 may be independently operable. For example, as illustrated with respect to the dispensing unit 301*a*, the piston 306*a* has been driven up in the dispensing chamber 302*a* so as to dispense almost all of the insects 104 from the dispensing chamber 302*a*. As illustrated with respect to the dispensing unit 301*b*, the piston 306*b* has been driven up to a different level in the dispensing chamber 302*b*. As illustrated with respect to the dispensing unit 301*c*, the piston 306*c* has not been driven up into the dispensing chamber 302*c*. Similarly, the gates 324 may be independently operable, e.g., the gate 324*c* is closed and the gates 324*a*, 324*b* are partially open. In some examples, the dispensing units 301 may be distributed in any suitable manner (e.g., in a radial configuration, a square configuration, and in any other configuration).

In some examples, operation of the dispensing units 301 may be coordinated. For example, the dispensing units 301*a*, 301*b*, and 301*c*, may be configured to dispense insects 104 at the same rate and at the same time (e.g., the pistons 306 may move within the dispensing chambers 302 at the same rate and from the same starting positions). In some examples, the insect storage and dispensing system 300 may be configured to dispense insects 104 at some global dispensing rate that is represents the aggregate dispensing rate of all, or some portion, of the dispensing units 301*a*, 301*b*, and 301*c* operating at different dispensing rates.

FIG. 4 illustrates an insect storage and dispensing cartridge 400 for use in an insect storage and dispensing system, according to at least one example. To use, the dispensing cartridge 400 is filled with incapacitated insects, loaded into a dispensing chamber, and a piston presses the insects out of the dispensing cartridge 400, such as into the exit chamber 108. However, unlike the dispensing chamber 102 of FIG. 1, the dispensing cartridge 400 is small, subdivided, and can be filled elsewhere, and then loaded into the full dispensing system, rather than having to manually load insects into dispensing chambers of the dispensing system.

As introduced above, the dispensing cartridge 400 can be loaded with insects 104 in a laboratory after the insects 104 have been raised in the laboratory. The dispensing cartridge 400 is then used to transport the insects 104. The dispensing cartridge 400 can also include a chilling sheath to cool the insects 104 within the dispensing cartridge 400. Whether or not the dispensing cartridge includes a chilling sheath, the dispensing cartridge 400 may be loadable into a chilling unit (e.g., a freezer or other device to cool the dispensing cartridge 400) to chill the insects 104. In some examples, the insects 104 are chilled as they are loaded into the dispensing cartridge 400.

The dispensing cartridge 400 includes a container 408. The container 408 includes a top opening 410, a bottom opening 412, and an interior wall that defines an interior volume. The container 408 includes a plurality of dividers 402 (e.g., 402*a*-402*c*) arranged within the container 408. The plurality of dividers 402 define a plurality of compartments 404 (e.g., 404*a*-404*d*). In some examples, the dividers 402 are supported by a support shaft 406 that extends longitudinally within the container 408. The support shaft 406 can be formed from a solid shaft, a hollow tube, or a set of hollow tubes. The construction of the support shaft 406 may depend on the desired function of the support shaft 406 described below. The dividers 402 extend from the support shaft 406 to interior walls of the container 408. In this manner, the compartments 404 are separate from each other such that an insect from one compartment 404 cannot access one of the other compartments 404. The dividers 402 can be formed as mesh screens or as solid surfaces. The dividers 402 include seals, e.g., similar to flexible piston ring 112, disposed at their exterior edges to provide insect-proof seals between the dividers 402 and an interior wall of the container 102. This may prevent insects from moving between compartments 404 while in the container 408.

In some examples, the support shaft 406 is configured to apply heat to an interior volume of the container 408, provide gas to the interior volume of the container 408, provide cooling to the interior volume of the container 408, and/or control humidity in the interior volume of the container 408 through connection(s) with the air movement system 128, the revival system 126, and/or the humidity control system 136. For example, to apply heat (e.g., for revival), the support shaft 406 can include one or more openings through which warmed air can from the revival system 126. In some examples, the support shaft includes its own independent heat source such as an electrical heating element. To provide gas (e.g., for sedation and/or revival), the support shaft 406 can include one or more openings through which gas can flow from the revival system 126 and into the container 408. To provide cooling (e.g., for sedation), the support shaft 406 can itself be cooled by a secondary cooling device and/or may include one or more openings through which cool air can flow into the container 408 from the air movement system 128 and/or humidity control system 136. To control humidity, the support shaft 406 can include one or more openings through which humidified or dehumidified air can flow from the humidity control system 136. The openings in the support shaft 406 can be screened to avoid movement of the insects 104 through the openings.

In some examples, the dividers 402, which define the compartments 404 in a stacked configuration, can be collapsed on top of each other to reduce the volume of the respective compartments 404. Such collapsing may be desirable to reduce extra volume in the compartments 404 and thereby increase insect packing density. For example, insects 404 in an active state can be loaded into the compartments 404 while the volume of the compartments is large. Following loading, the insects 104 can be sedated or otherwise incapacitated (e.g., via chilling, gas deprivation, etc.). With the container 408 in an upright orientation such as illustrated in FIG. 4, the sedated insects 104 will come to rest on top surfaces of the dividers 402 (e.g., floors of the compartments 404). The dividers 402 can then be collapsed into each other in order to compress the volume of the each compartment 404 to form a one-insect thick layer of insect 104. For example, all of the dividers 402 can move toward the plunger bottom 414, with the divider 402c traveling the furthest distance and the divider 402a traveling the shortest distance so as to keep the volumes of the compartments consistently smaller. In some examples, the dividers 402 can collapse on top of each other in an accordion-like fashion with both 402a and 402c traveling toward each other. Such loading can also be performed with the container 408 in a different orientation (e.g., on its side).

In some examples, the container 408 and/or the shaft 406 is/are configured to maintain elevations within the container 408 of the dividers 402. For example, notches can be provided in the shaft 406 that correspond to a loading position of the dividers 402 and sedated position of the dividers 402.

In some examples, the compartments 404 are loaded sequentially beginning with the compartment 404a. For example, with all of the dividers 402 removed, a first set of active insects 104 can be loaded into the container 408. These insects 104 can be sedated such that they fall and rest on interior-facing surface of the plunger bottom 414. The divider 402a can then be loaded into the container 408 and translated within the container 408 toward the insects 104 resting on the interior-facing surface of the plunger bottom 414 to define the compartment 404a in a compressed state. Next, a second set of insects 104 can be loaded into the container 408 and sedated such that the second set of insects 104 fall and rest on a top surface of the divider 402a. The divider 402b can then be loaded into the container 408 and translated within the container 408 toward the insects 104 resting on the top surface of the divider 402b to define the compartment 404b in a compressed state. The remaining N number of compartments 404 can be loaded in the manner previously described. Such loading can also be performed with the container 408 in a different orientation (e.g., on its side).

In some examples, the dispensing cartridge 400 includes the plunger bottom 414 and a cap 416. The plunger bottom 414 may be configured to move longitudinally within the container 408 to translate the dividers 402 within the container 408. Longitudinal movement is not limited to movement in an orthogonal direction As described herein, the dispensing cartridge 400 can also be loaded into a dispensing system. The dispensing system can be configured to drive the plunger bottom 414 longitudinally within the container 408 so as to expose the compartments 404 through the top opening 410. In some examples, the dispensing system includes a ratchet rod dispensing gun (e.g., similar to a caulk gun) that receives the dispensing cartridge 400 and is configured to dispense the insects 104 from the container 408. In some examples, the dispensing cartridge 400 is configured to engage with the piston 106, which is part of a dispensing system.

The plunger bottom 414 may be configured similar to the piston 106. In particular, the plunger bottom 414 may include a flexible piston ring 112 to ensure a smooth connection between the plunger bottom 414 and the interior wall of the container 408. In some examples, the dividers 402 also include some sort of flexible material along their perimeters so as to create a smooth connection between the perimeters of the dividers 402 and the interior wall of the container 408.

In some examples, instead of or in addition to the plunger bottom 414, the dispensing cartridge includes a solid bottom. In this example, removing the insects 104 may include translating the entire container 408 with respect to a dispensing chamber.

The cap 416 is removably attachable to the container 408. For example, the cap 416 can be screwable onto the container 408. When it comes time to dispense the insects 104, the cap 416 is removed so as to expose the insects 104 within the compartment 404d to air outside the dispensing cartridge 400. Once the insects 104 in the compartment 404d have been removed, the plunger bottom 414 is moved toward the top opening 410 so as expose the insects 104 within compartment 404c and so on and so forth until all of the insects 104 have been removed from the dispensing cartridge 400.

Figure 5:
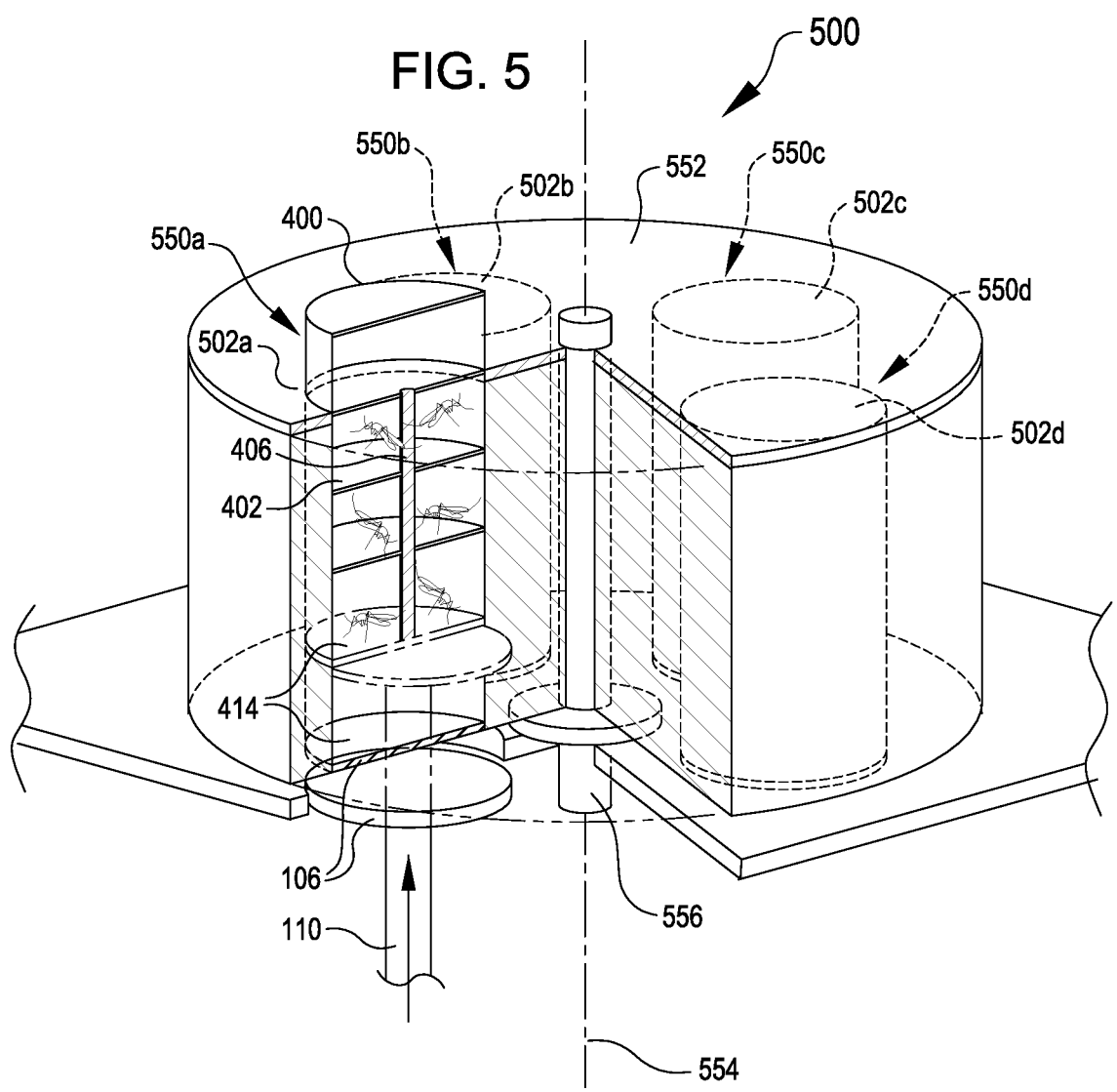
FIG. 5 illustrates an insect dispensing system including a plurality of dispensing chambers arranged in a rotary configuration, according to at least one example.

FIG. 5 illustrates dispensing system 500 including a plurality of dispensing units 550 arranged in a rotary dispensing configuration, according to at least one example. The dispensing units 550 may include dispensing chambers 502 configured to receive dispensing cartridges such as the dispensing cartridge 400, which have been pre-loaded with insects 104. In some examples, the insects 104 are held directly in the dispensing chambers 502 without using the dispensing cartridges 400. In some examples, the dispensing system includes a cylinder 552 which retains the dispensing units 550. The cylinder 552 may revolve around a central axis 554 extending along an alignment shaft 556. The alignment shaft 556 may align the cylinder 552 with the piston 106 and the connecting rod 110.

The cylinder 552 revolves about the central axis 554 to bring each individual dispensing unit 550 into alignment with the piston 106 for dispensing the insects 104 from the dispensing cartridge 400 and/or the dispensing chamber 502. After one of the dispensing cartridges 400 or dispensing chambers 502 has been emptied, the cylinder 552 rotates and indexes by one dispensing unit 550 in order to present the next dispensing unit 550 to the piston 106. The insects 104 may be removed from the dispensing cartridge 400 in the manner described herein. For example, the piston 106 can be used to drive the dispensing cartridge 400 out of a top opening of the dispensing chamber 502a. In other examples, the piston 106 can be used to drive an interior portion of the dispensing cartridge 400 (e.g., the dividers 402 and the support shaft 406) out of the top opening of the dispensing chamber 502a. In some examples, the dispensing system 500 is implemented without using the dispensing cartridges 400. For example, the insects 104 may be loaded directly into the dispensing chambers 502 and unloaded in the manner described with reference to FIGS. 1 and 2.

FIG. 6 illustrates dispensing system 600 including a plurality of dispensing units 650 arranged in a linear dispensing configuration, according to at least one example. The dispensing units 650 may include dispensing chambers 602 configured to receive dispensing cartridges such as the dispensing cartridge 400, which have been pre-loaded with insects 104. In some examples, the insects 104 are held directly in the dispensing chambers 602 without using the dispensing cartridges 400. The dispensing system 600 includes a linear array of dispensing units 650 held in a magazine 658. The magazine 658 can be indexed to align the dispensing units 650 with the piston 106. In some examples, the piston 106 is indexed to align with the individual dispensing units 650 of the magazine 658. In some examples, the magazine 658 can be loaded into a dispensing device that includes the piston 106.

In some examples, to dispense the insects 104 of a dispensing cartridge 400, the magazine 658 is moved into alignment with the piston 106 for dispensing the insects 104 from the dispensing cartridge 400 and/or the dispensing chamber 602. After one of the dispensing cartridges 400 or dispensing chambers 602 has been emptied, the magazine 658 moves and indexes by one dispensing unit 650 in order to present the next dispensing unit 650 to the piston 106. The insects 104 may be removed from the dispensing cartridge 400 in the manner described herein. For example, the piston 106 can be used to drive the dispensing cartridge 400 out of a top opening of the dispensing chamber 602a. In other examples, the piston 106 can be used to drive an interior portion of the dispensing cartridge 400 (e.g., the dividers 402 and the support shaft 406) out of the top opening of the dispensing chamber 602a. In some examples, the dispensing system 600 is implemented without using the dispensing cartridges 400. For example, the insects 104 may be loaded directly into the dispensing chambers 602 and unloaded in the manner described with reference to FIGS. 1 and 2.

FIGS. 7A-7C illustrate an insect storage and dispensing system 700, respectively, in a first state of operation, a second state of operation, and a third state of operation, according to at least one example.

The insect storage and dispensing system 700 includes a dispensing chamber 702, a piston 706, a connecting rod 710, a dispensing cartridge 400, a gate 724, and a chamber outlet 726 (e.g., an insect release opening). The dispensing cartridge 400 includes a plurality of dividers 402 that define a plurality of compartments 404. The compartments 404 may be separate and distinct from each other. As illustrated, the insect storage and dispensing system 700 may be aligned horizontally, vertically aligned, or aligned in any other manner.

In FIG. 7A, the dispensing cartridge 400, which has been previously loaded with insects 104, is loaded into the dispensing chamber 702. To load the dispensing cartridge 400, the piston 706 may be drawn away from the chamber outlet 726. While the dispensing cartridge 400 is illustrated with a one insect 104 in each compartment 404, it should be understood that many insects 104 may be loaded into each compartment 404. In FIG. 7A, the gate 724 is closed such that the insects 104 in the compartment 404d are unable to exit the dispensing cartridge 400.

In FIG. 7B, the gate 724 has been opened to allow the insects 104 in the compartment 404d to exit the compartment 404d via the chamber outlet 726 and a corresponding outlet of the compartment 404d. As the insects 104 fall through this corresponding outlet and the chamber outlet 726 toward ramp 728, the air movement system 128 and/or the revival system 126 may function to blow and/or warm the insects 104 in order to revive them from the chilled/sedated state.

In FIG. 7C, the piston 106 has been driven to translate the dispensing cartridge 400 with respect to the dispensing chamber 702. This may present a corresponding opening of the compartment 404c to the chamber outlet 726. As the insects 104 from the compartment 404c fall through this corresponding outlet and the chamber outlet 726 toward ramp 728, the air movement system 128 and/or the revival system 126 may function to blow and/or warm the insects 104 in order to revive them from the chilled/sedated state.

FIG. 8 illustrates an example process 800 for dispensing insects, according to at least one example. The process 800 is described with respect to the system 100 shown in FIG. 1, but can be performed using any suitable insect storage and dispensing system according to this disclosure.

The process 800 may begin at 802 by loading a plurality of insects into a dispensing chamber 102. In this example, the insects have been incapacitated by chilling them before loading them into the dispensing chamber 102. In some examples, however, the insects may be chilled within the dispensing chamber. However, other incapacitation techniques may be employed, such as inducing hypoxia, etc. The dispensing chamber 102 may be a cylinder as shown in FIG. 1, or a dispensing cartridge, such as the dispensing cartridge 400 shown in FIG. 4. In examples where the insects are loaded into a dispensing cartridge, the dispensing cartridge is then inserted into the cylinder 102 or into another dispensing system according to this disclosure.

At 804, the process 800 may include dispensing a first portion of the plurality of insects from the dispensing chamber 102 by moving the piston 106 from a first position to a second position. In an example employing a dispensing cartridge 400, the first portion of the insects may correspond to those held within a first compartment of the dispensing cartridge 500. In some examples, a distance between the first position and the second position may correspond to a height of the first compartment.

In some examples, dispensing the first portion of the plurality of insects includes warming the first portion of the plurality of insects using a revival system, such as the revival system 126 shown in FIG. 1.

In some examples, dispensing the first portion of the plurality of insects includes blowing or sucking the first portion of the plurality of insects using an air movement system, such as the air movement system 128 shown in FIG. 1.

In some examples, dispensing the first portion of the plurality of insects includes causing the first portion to move through an exit chamber (e.g., in an inlet and out an outlet), such as the exit chamber 118 show in FIG. 1.

In some examples, the process 800 may further include, prior to dispensing the first portion, opening a gate 124 so as to expose an interior volume of the dispensing chamber 102, the first portion of the plurality of insects being disposed within the interior volume.

In some examples, the process 800 may further include counting the first portion of the plurality of insects during dispensing of the first portion of the plurality of insects. This may be achieved, for example, using the insect counting system 132 shown in FIG. 1.

FIG. 9 illustrates an example process 900 for dispensing insects, according to at least one example. The process 900 is described with respect to the system 700 shown in FIG. 7, but can be performed using any suitable insect storage and dispensing system according to this disclosure.

Figure 4:
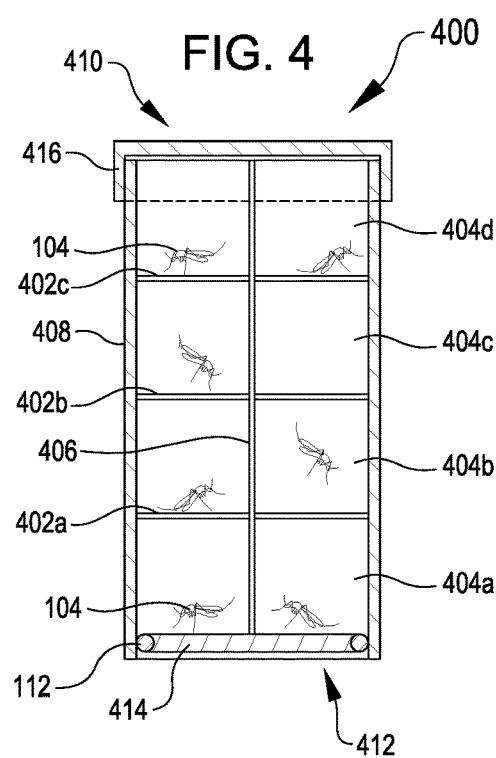
FIG. 4 illustrates an insect storage and dispensing cartridge for use in an insect storage and dispensing system, according to at least one example.

The process 900 may begin at 902 by loading a plurality of insects into a container such as the dispensing cartridge 400 shown in FIG. 4. The insects can be chilled or otherwise sedated prior to being loaded into the container, or may be chilled or otherwise sedated after loading. As the dispensing cartridge 400 may include multiple compartments 404, loading the plurality of insects can include loading the plurality of insects into the multiple compartments 404.

At 904, the process 900 may include loading the container into a dispensing chamber, such as the dispensing chamber 702 shown in FIG. 7. In other examples, the container can be loaded into different dispensing chambers such as those shown in FIGS. 1, 3, 5, and 6. Loading the container into the dispensing chamber can include placing the container in the dispensing chamber. When the system includes more than one dispensing chamber such as the multiple dispensing units 301, 550, and 650, more than one container can be loaded into the multiple dispensing chambers.

At 906, the process 900 may include dispensing a first portion of the plurality of insects from the container by at least: translating the container with respect to the dispensing chamber, and applying at least one of heat, or Oxygen, or air flow to first portion of the plurality of insects. Translating the container with respect to the dispensing chamber can be achieved using a piston such as the piston 706 shown in FIG. 7, that drives the container within the dispensing chamber. In some examples, the container can include one or more openings that, when aligned with an opening such as the insect opening 626, create a pathway for the insects 104 to exit the container 400.

Applying heat to the first portion of the plurality of insects may be achieved using a revival system, such as the revival system 126 shown in FIG. 1. Applying air flow to the first portion of the plurality of insects may be achieved using an air movement system, such as the air movement system 128 shown in FIG. 1.

Dispensing the insects from the container can include dispensing the insects into an exit container, such as the exit container 118.

In some examples, the container is a reusable dispensing cartridge. The plurality of insects can include mosquitoes or any other suitable insect. In some examples, a dispensing rate of dispensing the plurality of insects is based at least in part on a translation rate of the container with respect to the dispensing chamber and a flow rate of the air flow.

FIG. 10 illustrates an example process 100 for loading insects, according to at least one example. The process 1000 is described with respect to the insect storage and dispensing cartridge 400 shown in FIG. 4 including compartments in a stacked configuration, but can be performed using any suitable insect storage and dispensing cartridge according to this disclosure.

The process 1000 may begin at 1002 by loading a plurality of active insects into an interior volume of a container including an interior wall that defines the interior volume. For example, the active insects can be loaded in the dispensing cartridge 400 shown in FIG. 4. The insects may be active in the sense that they are capable of movement such as walking and flying. Loading the insects may be achieved by blowing the insects into the container. As the container may include multiple compartments, loading can include loading the insects into more than one compartment of the container. In some examples, the insects are loaded into the multiple compartments in parallel or in series.

At 1004, the process 1000 may include incapacitating at least a portion of the plurality of insects located within the interior volume of the container. For example, this can be achieved by depriving the insects of Oxygen, chilling the insects, or performing any other suitable incapacitation technique. As the container may include multiple compartments, incapacitating the insects can include incapacitating the insects in more than one compartment of the container. In some examples, the insects of one compartment are incapacitated after being loaded, but before other insects are loaded into other compartments. In other examples, the insects of multiple compartments are incapacitated at the same time.

At 1006, the process 100 may include compressing the portion of the plurality of insects by reducing the interior volume of the container. In some examples, this can include moving a divider such as the divider 402 within the container to reduce the volume of the container. In some examples, the compressing is performed after the insects have been sedated and are resting in the container. In some examples, the number of insects loaded into the container is metered such that, when the insects are sedated, a one-insect thick layer is formed. This may be desirable to avoid a three dimensional entanglement of insects. As the container may include multiple compartments, compressing can include compressing each of the multiple compartments to reduce the interior volume of each of the compartments. In some examples, the dividers of the container are movable so as to change the volume of the compartments within the container.

In some examples, the process 1000 is repeated for each compartment of a multi-compartment container at least until the container is full of many layers of sedated insects separated by dividers. Once loaded, the container can be loaded into one of the storage and dispensing systems described herein for revival and dispensing of the insects.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:

1. A system, comprising:
  a dispensing cartridge comprising at least one first wall defining a first interior volume for retaining a plurality of adult insects;
  a dispensing container comprising at least one second wall defining a second interior volume for retaining the dispensing cartridge, the dispensing container comprising a first opening at a first end and a second opening at a second end; and
  a piston comprising a top face, the piston extending through the first opening and into the dispensing container so as to physically contact the dispensing cartridge, wherein longitudinal movement of the piston through the second interior volume and toward the second opening causes translation of the dispensing cartridge through the second interior volume and dispenses a portion of the plurality of adult insects from the dispensing cartridge when the plurality of adult insects is retained in the dispensing cartridge.

2. The system of claim 1, further comprising an air movement system disposed adjacent the second opening of the dispensing container, the air movement system configured to cause an air stream to flow across the second opening to remove, from the dispensing cartridge, portions of the plurality of adult insects that are presented at the second opening by the longitudinal movement of the piston.

3. The system of claim 2, wherein the air movement system comprises a fan, a Venturi tube, or an aspirator device.

4. The system of claim 1, further comprising a movable gate positioned at the second end so as to selectively occlude the second opening.

5. The system of claim 4, wherein the movable gate is slidable between a first position and a second position so as to occlude a larger portion of the second opening in the first position and a smaller portion of the second opening in the second position.

6. The system of claim 1, further comprising a revival system disposed adjacent the second opening of the dispensing container, the revival system configured to revive portions of the plurality of adult insects that are presented at the second opening by the longitudinal movement of the piston.

7. The system of claim 1, further comprising a cooling sheath configured to chill the plurality of adult insects within the dispensing cartridge.

8. A system, comprising:
  an exit chamber comprising a structure that defines a first interior volume, wherein the exit chamber is oriented longitudinally along a first axis and comprises an inlet and an outlet; and
  a dispensing system, comprising:
    a dispensing container comprising at least one wall defining a second interior volume for retaining a plurality of adult insects, the dispensing container oriented along a second axis that is substantially perpendicular to the first axis and comprising a first opening at a first end and a second opening at a second end opposite the first end, wherein the dispensing container is oriented with respect to the exit chamber to define an insect pathway between the second opening and the inlet; and
    a piston comprising a top face, the piston extending through the first opening and into the dispensing container so as to expose the top face to the second interior volume, wherein longitudinal movement of the piston along the second axis and through the second interior volume and toward the second opening causes a portion of the plurality of adult insects to move from the dispensing container into the exit chamber via the insect pathway when the plurality of adult insects is retained in the dispensing container.

9. The system of claim 8, further comprising an air movement system disposed adjacent the second opening of the dispensing container, the air movement system configured to cause an air stream to flow across the second opening to blow portions of the plurality of adult insects out of the exit chamber via the outlet.

10. The system of claim 9, wherein the air movement system comprises a fan, a Venturi tube, or an aspirator device.

11. The system of claim 8, further comprising a movable gate positioned at the second end so as to selectively occlude the second opening.

12. The system of claim 11, wherein the movable gate is slidable between a first position and a second position so as to occlude a larger portion of the second opening in the first position and a smaller portion of the second opening in the second position.

13. The system of claim 8, further comprising a revival system disposed adjacent the second opening of the dispensing container, the revival system configured to revive portions of the plurality of adult insects that are presented at the second opening by the longitudinal movement of the piston.

14. The system of claim 8, wherein the dispensing container comprises a dispensing cartridge defining an interior volume to receive the plurality of adult insects and to be inserted within the dispensing container.

15. The system of claim 8, further comprising a cooling sheath configured to chill the plurality of adult insects within the dispensing container.

16. The system of claim 8, further comprising at least one of a vibration system configured to apply vibration to the exit chamber, or a humidity control system configured to provide humidification or dehumidification to the first interior volume.

17. The system of claim 1, wherein the dispensing cartridge comprises a plurality of distinct chambers each configured to retain individual portions of adult insects of the plurality of adult insects, and wherein the translation of the dispensing cartridge through the second interior volume selectively dispenses the individual portions of adult insects.

* * * * *